United States Patent [19]

Iqbal et al.

[11] Patent Number: 4,885,100

[45] Date of Patent: Dec. 5, 1989

[54] TRIS(ISONITRILE)COPPER(I) ADDUCTS FOR PREPARING RADIONUCLIDE COMPLEXES

[75] Inventors: Tahir Iqbal, Lowell, Mass.; John H. Cain, Jr., Merrimack, N.H.; Jack J. Slosky, Shrewsbury, Mass.

[73] Assignee: E. I. Du Pont de Nemours and Company, Wilmington, Del.

[21] Appl. No.: 95,924

[22] Filed: Sep. 11, 1987

[51] Int. Cl.$^4$ .......................... C07F 13/00; C07F 1/08; C07C 119/02
[52] U.S. Cl. ............................................ 252/1; 556/7; 556/13; 556/110; 558/302; 534/14; 424/1.1
[58] Field of Search .......................... 424/1.1; 534/14; 558/302; 556/7, 13, 110; 252/1

[56] References Cited

U.S. PATENT DOCUMENTS

| | | | |
|---|---|---|---|
| 3,117,938 | 1/1964 | Byrrus | 556/110 X |
| 3,197,493 | 7/1965 | Allison | 558/302 X |
| 4,451,665 | 5/1984 | Nugent | 556/13 X |

FOREIGN PATENT DOCUMENTS

| | | | |
|---|---|---|---|
| 0211424 | 2/1987 | European Pat. Off. | 424/1.1 |
| 0233368 | 8/1987 | European Pat. Off. | 424/1.1 |

*Primary Examiner*—John S. Maples

[57] ABSTRACT

Tris(isonitrile)copper(I) complex salts with anions selected from $BF_4$, $PF_6$, $ClO_4$, I, Br, Cl and $CF_3COO$ are useful in preparing radionuclide complexes rapidly at room temperature. Preferred isonitrile ligands are ether isonitriles. The tris(isonitrile)copper(I) adducts enable technetium complexes, such as those of Tc99m, to be prepared easily just prior to their use as imaging agents.

11 Claims, No Drawings

TRIS(ISONITRILE)COPPER(I) ADDUCTS FOR PREPARING RADIONUCLIDE COMPLEXES

BACKGROUND OF THE INVENTION

1. Field of Invention

This invention relates to tris(isonitrile)copper(I) adducts, their preparation, kits containing them, and methods of using them to prepare technetium complexes.

2. General Background and Prior Art

Isonitrile complexes of various radionuclides and their use as imaging agents are known in the art as described, for example by Jones et al. in U.S. Pat. No. 4,452,774, issued June 5, 1984. The complexes described by Jones, et al are of the general formula:

$$[A((CN)_xR)_yB_zB'_{z'}]^n$$

in which A is a radionuclide selected from radioactive isotopes of Tc, Ru, Co, Pt, Fe, Os, Ir, W, Re, Cr, Mo, Mn, Ni, Rh, Pd, Nb, and Ta, for example, Tc99m, Tc99, $^{97}$Ru, $^{51}$Cr, $^{57}$Co, $^{188}$Re and $^{191}$Os; $(CN)_xR$ is a monodentate or polydentate isonitrile ligand bonded to the radionuclide through the carbon atom of the CN group; R is an organic radical; B and B' are independently selected from other ligands well known to those skilled in the art that result in isonitrile complexes, including solvents such as water, chloro and bromo groups, and ligands comprising one or more neutral donor atoms capable of forming bonds with said radionuclide; x and y are each independently integers from 1 to 8; z and z' are each independently 0 or an integer from 1 to 7; with the proviso that (xy)+z+z' is less than or equal to 8; and n indicates the charge of the complex and can be 0 (neutral), or a positive or negative integer the value of which depends upon the valence state of A, and the charges on R, B and B'. Any desired counterion can be present as required by the charge on the complex with the proviso that such counterion must be pharmaceutically acceptable if the complex is to be used in vivo.

In the above formula, R is an organic radical that can be aliphatic or aromatic and may be substituted with a variety of groups which may or may not be charged. When the organic radical R carries a charged substituent group, the charge on the resultant complex is the summation of the charges of the ligands (R, B and B') and the charge of the radionuclide. Among the aromatic R groups which may be present are phenyl, tolyl, xylyl, naphthyl, diphenyl and substituted aromatic groups containing such substituents as halo, e.g., chloro, bromo, iodo or fluoro; hydroxy, nitro, alkyl, alkoxy, etc.; among the aliphatic R groups which may be present are alkyl, preferably containing 1 to 20 carbon atoms, such as methyl, ethyl, n-propyl, isoprropyl, n-butyl, isobutyl, n-hexyl, 2-ethylhexyl, dodecyl, stearyl, etc. Substituent groups may also be present in the aliphatic groups, including among others the same substituent groups as those listed above for aromatic groups.

The complexes described by Jones et al. are described as being useful for visualizing cardiac tissue, detecting the presence of thrombi in the lung and associated areas of blood perfusion deficits, studying lung function, studying renal excretion, and imaging bone marrow and the hepatobiliary system.

In practice, the technetium complex of the simple hydrocarbon isonitriles such as t-butyliso-nitrile preferred by Jones et al. have demonstrated somewhat high concentration in the lung and liver in humans. [Holman, et al., *J. Nucl. Med.*, 25, 1380(1984)].

Other isonitrile complexes of radionuclides are described by Jones et al. in European Patent Appln. 213,945 published Mar. 11, 1987. The isonitrile ligands described therein have the formula:

(CNX)R, where X is a lower alkyl group having 1 to 4 carbon atoms, R is selected from the group consisting of COOR$_1$ and CONR$^2$R$^3$; where R$^1$ can be H, a pharmaceutically acceptable cation, or a substituted or unsubstituted alkyl group having 1 to 4 carbon atoms, and R$^2$ and R$^3$ can be the same or different, results in a complex having the general advantages of the isonitrile radionuclide complexes of U.S. Pat. No. 4,452,774, but having generally superior properties with respect to liver clearance or lung clearance. Consequently, these complexes can allow earlier imaging, and/or better imaging of bodily tissues and organs than their corresponding parent compounds. Described are coordination complexes of Tc, Ru, Co, Pt or Re with the above isonitrile ligands.

Additional isonitrile complexes of radionuclides are described in coassigned U.S. patent application Ser. No. 056,003, filed June 1, 1987 (NN-0181-B), in the names of Bergstein and Subramanyan. The isonitrile ligands described therein are ether-substituted isonitriles of the formula:

$$\text{CN-A-O-R} \quad \text{or} \quad \begin{array}{c} \text{CNAOR} \\ | \\ \text{OR}' \end{array}$$

$$\text{(I)} \quad\quad\quad \text{(Ia)}$$

wherein
  A is a straight or branched chain alkyl group; and
  R and R' each independently is a straight or branched chain alkyl group or taken together are a straight or branched chain alkylene group, provided that:
    (1) the total number of carbon atoms in A plus R in formula (I) is 4 to 6, provided further that when the total number of carbon atoms is 6, then the carbon atom alpha to the isonitrile group is a quaternary carbon, and
    (2) the total number of carbon atoms in A plus R plus R' in formula (Ia) is 4 to 9.

The further evaluation of isonitrile Tc99m complexes of U.S. Pat. No. 4,452,774 is described by E. Deutsch et al., *J. Nucl. Med.*, 27, 409 (1986); M. N. Khalil et al., *Nucl. Med. Cummun.*, 6, 615 (1985); A. G. Jones et al., *J. Nucl. Med.*, 25, 1350 (1984); A. G. Jones et al., *Int. J. Nucl. Med. Biol.*, 11, 225 (1984); and A. Davison et al., *Inorg. Chem.*, 22, 2798 (1983).

One difficulty in preparing isonitrile complexes of radionuclides is that many isonitriles are extremely volatile; thus, the manufacturing of lyophilized kits for commercial purposes is not possible. Published European Patent Appln. No. 211,424, published Feb. 25, 1987, addresses this problem by preparing soluble isonitrile complexes of metals such as Cu, Mo, Pd, Co, Ni, Cr, Ag and Rh and then reacting them with the desired radionuclide. The pair of metals chosen is such that the non-radioactive metal is readily displaceable from its isonitrile complex in an appropriate media by the desired radionuclide, thus giving the desired radiopharmaceutical. The copper complexes described are (bis-isonitrile)phenanthroline and tetrakis-isonitrile complexes. A further difficulty occurs when such non-radioactive metal (e.g. Cu) isonitrile adducts are reacted with a desired radionuclide (e.g. Tc99m) to prepare a radiopharmaceutical. Many such adducts react with Tc99m at elevated temperatures to produce a radiopharmaceutical rapidly. The reaction at room temperature is slow and may take several hours to produce a high yield of the desired radiopharmaceutical.

SUMMARY OF THE INVENTION

According to the present invention, provided is a tris(isonitrile)copper(I) adduct with an anion selected from $BF_4$, $PF_6$, $ClO_4$, I, Br, Cl and $CF_3COO$. Such an adduct reacts easily and rapidly with radionuclides such as Tc99m at room temperature to prepare radiopharmaceuticals in good yields.

Further provided is a kit for preparing a complex of an isonitrile ligand and a radionuclide which comprises a predetermined quantity of the aforesaid copper tris adduct and a predetermined quantity of a sterile, non-pyrogenic reducing agent capable of reducing a predetermined quantity of a predetermined radionuclide, preferably Tc99m.

Additionally provided is a process for preparing the aforesaid complex which comprises mixing in a suitable solvent the aforesaid copper tris adduct at room temperature with a radionuclide, preferably pertechnetate.

Also provided is a process for preparing the aforesaid adduct which comprises:
(1) reacting in a suitable solvent about one equivalent weight of:
  (a) a tetrakis(acetonitrile)copper(I) $BF_4$, $PF_6$, or $ClO_4$, or
  (b) cuprous iodide, bromide or chloride,
with about three equivalent weights respectively of:
  (a) a tetrakis(isonitrile) ligand)copper(I) $BF_4$, $PF_6$, or $ClO_4$, or
  (b) an isonitrile ligand; and
(2) removing the solvent to provide a solid copper tris product.

DETAILED DESCRIPTION OF THE INVENTION

The copper tris isonitrile adducts of the present invention can be prepared using any isonitrile ligand. Suitable isonitrile ligands include those having, for example, the formula CNR where R is an organic radical which can be aliphatic or aromatic and can be substituted with a variety of groups which may or may not be charged. Examples of suitable isonitrile ligands can be found in the abovementioned U.S. Pat. No. 4,452,774; Published European Pat. Appln. No. 213,945; and in U.S. Ser. No. 056,003, the disclosures of which are hereby incorporated by reference as described hereinbefore.

Tris(isonitrile)copper(I) tetrafluoroborates and perchlorates can be synthesized by the exchange of acetonitrile molecules in tetrakis(acetonitrile)copper(I) complexes, [Cu(CH$_3$CN)$_4$X], where X is $BF_4$, $PF_6$, or $ClO_4$ (preferably $BF_4$ or $ClO_4$), with isonitrile ligands contained in a complex of the formula [Cu(RNC)$_4$]X. Thus, when a suspension of one equivalent of [Cu(CH$_3$CN)$_4$]X in a chlorinated solvent such as chloroform is treated with three equivalents of [Cu(MIBI)$_4$X]*, and the solvent is completely removed, a quantitative yield of [Cu(MIBI)$_3$]X is obtained. These compounds are white crystalline solids at room temperature.
*(MIBI=2-Methoxyisobutyl isonitrile)

Tris(isonitrile)copper(I) iodides, bromides, or chlorides are prepared by reacting one equivalent of cuprous iodide, bromide or chloride with three equivalents of an isonitrile, such as MIBI, in chloroform at about 0° C. In this reaction, iodide is preferred.

The desired radiolabeled, isonitrile complexes are prepared by admixing a copper isonitrile adduct with a radioactive metal in suitable media at temperatures from room temperature to reflux temperatures or even higher. The radioactive metal (radionuclide) can be any of those described in U.S. Pat. No. 4,452,774 with technetium (Tc99m) being preferred. The desired labeled isonitrile complexes are isolable and can be obtained in high yields. In some cases the isonitrile can itself act as a reducing agent thus eliminating the need for an additional reducing agent. Additional reducing agents, when required or desired to speed up the reaction, are well known to those skilled in the art. Examples of such well-known reducing agents include a stannous salt such as stannous chloride (often used with the isonitrile adduct in the form of a kit), formamidine sulfinic acid, sodium dithionite, sodium bisulfite, hydroxylamine, ascorbic acid, and the like. The reaction is generally complete after about 1 minute to about 2 hours, depending upon the particular reagents employed and the conditions used.

In the case of technetium such as, for example Tc99 or Tc99m, an isonitrile complex is preferably made by mixing an appropriate reducing agent (capable of reducing technetium in aqueous medium) and an appropriate copper isonitrile adduct then adding pertechnetate. Alternatively, the copper isonitrile adduct and pertechnetate are mixed, then reductant added. For example, when [Cu(MIBI)$_3$]X, where X is $BF_4$, $PF_6$, $ClO_4$, iodide, bromide or chloride is reacted with $^{99m}TcO_4^-$ in aqueous media in the presence of a suitable reducing agent (e.g., SnCl$_2$/cysteine), high yields of [$^{99m}$Tc(MIBI)$_6$]$^+$ are obtained. The reaction takes place at room temperature and greater than 90% labeling is achieved within 5–45 min. The formation of [$^{99m}$Tc(MIBI)$_6$]$^+$ is evidenced by radioanalytic thin layer chromatography (TLC) which shows greater than 90% labeling within 30 minutes. The difference in the reactivities of tris and tetrakis complexes is readily apparent when one compares the radioanalytical TLC of [$^{99m}$Tc(MIBI)$_6$]$^+$ derived from these compounds at room temperature after twenty minutes reaction with pertechnetate.

An excess of the copper isonitrile adduct, up to 50–100 fold molar excess or more, and an excess of reducing agent, can be used in the complexing reaction to ensure maximum yield from the technetium. Following the reaction, the desired complex can be separated from the reaction mixture, if required, for example by crystallization or precipitation or by conventional chromatography or ion exchange chromatography; see U.S. Pat. No. 4,452,774, supra, the disclosure of which is hereby incorporated by reference.

Kits in accord with the present invention comprise a sterile, non-pyrogenic, copper(I)tris adduct of an isonitrile ligand and an anion selected from $BF_4$, $PF_6$, $ClO_4$, I, Br and Cl, and, if required, a quantity of a reducing agent for reducing a preselected radionuclide. Preferably, such kits contain a predetermined quantity of the sterile copper isonitrile adduct and a predetermined quantity of a sterile reducing agent capable of reducing a predetermined quantity of the preselected radionuclide. It is also preferred that the copper isonitrile adduct and reducing agent be lyophilized, when possible, to facilitate storage stability. If lyophilization is not practical, the kits can be stored frozen. The copper isonitrile adduct and reducing agent are preferably contained in sealed, non-pyrogenic, sterilized containers.

The invention can be further understood by the following examples in which parts and percentages are by weight unless otherwise indicated.

EXAMPLE 1

Preparation of [Cu(MIBI)$_3$]BF$_4$

A freshly prepared sample of [Cu(CH$_3$CN)$_4$]BF$_4$ (0.533 g, 1.69 mmol) was suspended in 20 ml of chloroform. To this was added 3.064 g (5.08 mmol) of [Cu(MIBI)$_4$]BF$_4$. The reaction mixture was stirred at room temperature for 15 min. to give a clear solution. The solvent was then evaporated completely under reduced pressure to give a semi-solid residue which was again dissolved in 20 ml of chloroform. The solvent was once again evaporated under reduced pressure with the product beginning to solidify under high vacuum in about 2 hour. The crude product was then dissolved in 25 ml of chloroform and to this 25 ml of ethylacetate was added. The resulting clear solution was diluted with ethyl ether until it became cloudy. It was warmed to about 30° C. and more ether was added to obtain a cloudy solution. The mixture was first allowed to cool to room temperature and was then chilled in a refrigerator overnight. The crystalline product was separated by filtration; (2.70 g, 81% yield), m.p. 112°-113° C.

EXAMPLE 2

Preparation of [Cu(MIBI)$_3$]ClO$_4$

A freshly prepared sample of [Cu(CH$_3$CN)$_4$]ClO$_4$ (0.401 g, 1.226 mmol) was suspended in 20 ml of chloroform. To this was added 2.262 g (3.678 mmol) of [Cu(MIBI)$_4$]ClO$_4$. After the reaction mixture was stirred for 15 minutes to give a clear solution, the solvent was then evaporated to dryness under reduced pressure. The residue was redissolved in 5 ml of chloroform and then the solvent was once again evaporated completely. This process was repeated two more times to afford 2.411 g (98% yield) of white solid; m.p. 68°-69° C.

EXAMPLE 3

Preparation of [Cu(MIBI)$_3$I]

To a stirred suspension of 3.040 g (16 mmol) of copper(I) iodide in 25 ml of chloroform, under a nitrogen atmosphere, at 0° C. was slowly added 5.424 g (48 mmol) of MIBI. The mixture was stirred until a clear solution resulted and then was diluted with diethyl ether until the solution became cloudy. The mixture was allowed to stand at room temperature overnight, after which the product was isolated by filtration. It was washed twice with ether and dried under vacuum, 6.488 g (77% yield), m.p. 85° C.

EXAMPLE 4

Technetium complexes were prepared by dissolving each of [Cu(MIBI)$_3$I] and [Cu(MIBI)$_3$]BF$_4$ (1-2 mg), mannitol (15-25 mg), sodium citrate dihydrate (2-3 mg), cysteine hydrochloride (1-2 mg) and stannous chloride (5-10 μL of a solution of 20-25 mg of SnCl$_2$.2H$_2$O in 10 ml of 0.01N HCl) in a 5 cc serum vial (pH 5-6). The vials were sealed and 20-30 mCi of $^{99m}$TcO$_4^-$ obtained by elution of a 99Mo/99mTc radionuclide generator was added. The vials were allowed to sit for 10-45 minutes at room temperature. The purity of the final product [Tc(MIBI)$_6$]$^+$ thus obtained was determined by radioanalytic thin layer chromatography on Whatman C-18 reversed-phase plates using a solvent mixture containing a 20% 0.5M aqueous ammonium acetate, 30% methanol, 40% acetonitrile and 10% tetrahydrofuran.

As a control, the same technetium complex was prepared as above using [Cu(MIBI)$_4$]BF$_4$ as the starting adduct, except the serum vial was placed in a 100° C. water bath for 15 minutes after addition of the pertechnetate.

The complexes were evaluated by determining the biodistribution of each in guinea pigs. Organ distribution of injected activity was determined at 0.5, 15, and 60 minutes post-injection. For each time-point, three guinea pigs were anesthetized with sodium pentabarbital (35 mg/kg ip) and injected with 0.1 ml of test material via the jugular vein. The injected dose of Tc99m isonitrile was 0.8-1 mCi. Upon sacrifice, the organs were removed and radioactivity was measured using either a Capintec dose calibrator or gamma well counter. The heart, lungs and liver were weighed. The distribution of radioactivity in the heart, lung, and liver for the complexes are illustrated in Table I below. It can readily be seen that the technetium-99m complexes prepared from tris(isonitrile)copper(I) adducts provide substantially the same imaging results as the complex prepared from the tetra(isonitrile)copper(I) adduct.

TABLE I

Guinea Pig Biodistribution of Tc99m vs. Time
% ID/GR*

| Complex Prepared From [Cu(MIBI)$_4$]BF$_4$ | | | |
| --- | --- | --- | --- |
| TIME POINT (MIN) | 0.5 | 15 | 60 |
| N | 3 | 3 | 3 |
| Blood | 0.718 +/− 0.1706 | 0.03 +/− 0.0003 | 0.009 +/− 0.0017 |
| Heart | 1.967 +/− 0.4242 | 1.522 +/− 0.2716 | 1.245 +/− 0.0791 |
| Lung | 1.149 +/− 0.2934 | 0.879 +/− 0.3778 | 0.374 +/− 0.1731 |
| Liver | 0.579 +/− 0.0305 | 0.628 +/− 0.1892 | 0.465 +/− 0.2326 |

| Complex Prepared From [Cu(MIBI)$_3$]BF$_4$ | | | |
| --- | --- | --- | --- |
| TIME POINT (MIN) | 0.5 | 15 | 60 |
| N | 3 | 3 | 3 |
| Blood | 0.646 +/− 0.0697 | 0.020 +/− 0.0021 | 0.014 +/− 0.0006 |
| Heart | 1.898 +/− 0.3666 | 1.155 +/− 0.1102 | 1.206 +/− 0.0879 |
| Lung | 0.918 +/− 0.1472 | 0.414 +/− 0.0647 | 0.335 +/− 0.0225 |
| Liver | 0.888 +/− 0.1945 | 0.751 +/− 0.0662 | 0.624 +/− 0.1217 |

| Complex Prepared From [Cu(MIBI)$_3$I] | | | |
| --- | --- | --- | --- |
| TIME POINT (MIN) | 0.5 | 15 | 60 |
| N | 3 | 3 | 3 |
| Blood | 0.874 +/− 0.1341 | 0.034 +/− 0.0056 | 0.020 +/− 0.0032 |
| Heart | 1.548 +/− 0.6038 | 1.480 +/− 0.1866 | 1.549 +/− 0.0970 |
| Lung | 1.118 +/− 0.1827 | 0.450 +/− | 0.445 +/− 0.1191 |

TABLE I-continued

Guinea Pig Biodistribution of Tc99m vs. Time
% ID/GR*

| | | .0982 | |
|---|---|---|---|
| Liver | 0.736 +/− 0.2603 | 0.732 +/− 0.1235 | 0.569 +/− 0.1749 |

*Percent injected dose per gram of tissue (mean +/− sample deviation).

What is claimed is:

1. A tris(isonitrile)copper(I) complex of the formula $$[Cu(R''NC)_3]X$$

wherein

X is an anion selected from $BF_4$, $PF_6$, $ClO_4$, I, Br, Cl and $CF_3COO$; and R'' is alkyl of 1–20 carbon atoms or has the formula:

$$-A-O-R \quad \text{or} \quad -A-OR \atop \phantom{-A-}OR'$$
$$(I) \qquad\qquad (Ia)$$

wherein

A is a straight or branched chain alkylene group; and

R and R' each independently is a straight or branched chain alkyl group or taken together are a straight or branched chain alkylene group, provided that:

(1) the total number of carbon atoms in A plus R in formula (I) is 4 to 6, provided further that when the total number of carbon atoms is 6, then the carbon atom alpha to the isonitrile group is a quanternary carbon, and (2) the total number of carbon atoms in A plus R plus R' in formula (Ia) is 4 to 9.

2. The adduct of claim 1 which is tris(1-isocyano-2-methoxy-2-methylpropane)copper(I)$BF_4$.

3. The adduct of claim 1 which is tris(1-isocyano-2-methoxy-2-methylpropane)copper(I)$ClO_4$.

4. The adduct of claim 1 which is tris(1-isocyano-2-methoxy-2-methylpropane)copper(I)I.

5. A kit for preparing a complex of an isonitrile ligand and a radionuclide comprising a predetermined quantity of an adduct of claim 1 and a predetermined quantity of a sterile, non-pyrogenic reducing agent capable of reducing a predetermined amount of a predetermined radionuclide.

6. A kit of claim 5 wherein said adduct and said reducing agent are lyophilized or frozen and said radionuclide is Tc99m.

7. A kit of claim 5 wherein the reducing agent is $SnCl_2$ or a mixture of $SnCl_2$ and cysteine.

8. A kit of claim 6 wherein said adduct is tris(1-isocyano-2-methoxy-2-methylpropane)copper(I)$BF_4$.

9. A kit of claim 6 wherein said adduct is tris(1-isocyano-2-methoxy-2-methylpropane)copper(I)$ClO_4$.

10. A kit of claim 6 wherein said adduct is tris(1-isocyano-2-methoxy-2-methylpropane)copper(I)I.

11. A kit of claim 6 wherein the reducing agent is $SnCl_2$ or a mixture of $SnCl_2$ and cysteine.

* * * * *